United States Patent [19]

Saito

[11] Patent Number: 6,159,991
[45] Date of Patent: Dec. 12, 2000

[54] PESTICIDAL COMPOSITION

[75] Inventor: Shigeru Saito, Toyonaka, Japan

[73] Assignee: Sumitomo Chemical Company, Limited, Osaka-fu, Japan

[21] Appl. No.: 09/306,453

[22] Filed: May 6, 1999

[30] Foreign Application Priority Data

Jun. 2, 1998 [JP] Japan .................... 10-152736

[51] Int. Cl.⁷ .......................... A01N 43/40; A01N 37/34; A01N 31/14
[52] U.S. Cl. .......................... 514/345; 514/521; 514/721
[58] Field of Search ........................... 514/345, 521, 514/721

[56] References Cited

FOREIGN PATENT DOCUMENTS 96 11909   4/1996   WIPO .

*Primary Examiner*—Allen J. Robinson
*Attorney, Agent, or Firm*—Birch, Stewart, Kolasch & Birch, LLP

[57] ABSTRACT

A pesticidal composition containing 3,5-dichloro-1-(3,3-dichloro-2-propenyloxy)-4-[3-(5-trifluoromethylpyridin-2-yloxy)propoxy]benzene of the formula:

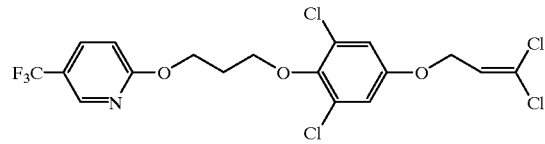

and a specific pyrethroid compound as active ingredients.

13 Claims, No Drawings

PESTICIDAL COMPOSITION

FILED OF INVENTION

The present invention relates to a pesticidal composition.

BACKGROUND OF THE INVENTION

Pyrethroid compounds have excellent pesticidal activity. In recent years, however, various kinds of pests have developed resistance to pyrethroid compounds, so that pest-control effects cannot be attained at a satisfactory level in certain cases. Thus, there has been a demand for the development of controlling agents which can exhibit excellent effects even against various kinds of pests having such developed resistance.

SUMMARY OF THE INVENTION

Under these circumstances, the present inventors have extensively studied. As a result, they have found that a pesticidal composition containing as active ingredients, 3,5-dichloro-1-(3,3-dichloro-2-propenyloxy)-4-[3-(5-trifluoromethylpyridin-2-yloxy)propoxy]benzene of the formula:

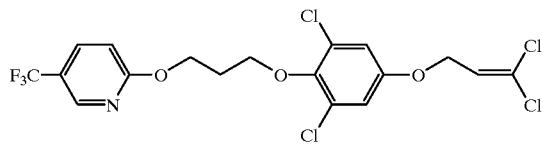

and a specific pyrethroid compound as recited below, can attain the effective control of both pyrethroid-resistant pests and pyrethroid-nonresistant pests and that their cooperative action is synergistic and therefore the application amount of pyrethroid compounds can be reduced as well as the development of pyrethroid resistance can be inhibited, thereby completing the present invention.

Thus, the present invention provides a pesticidal composition which comprises as active ingredients, 3,5-dichloro-1-(3,3-dichloro-2-propenyloxy)-4-[3-(5-trifluoromethylpyridin-2-yloxy)propoxy]benzene of the formula:

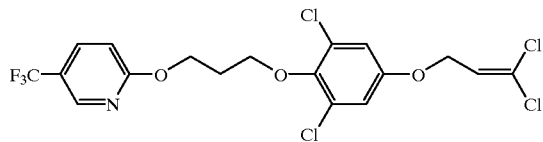

(hereinafter referred to as compound (I)) and a pyrethroid compound selected from the group consisting of α-cyano-3-phenoxybenzyl 2-(4-chlorophenyl)-3-methylbutyrate, α-cyano-3-phenoxybenzyl 2,2,3,3-tetramethylcyclopropane-carboxylate, α-cyano-3-phenoxybenzyl 3-(2,2-dichlorovinyl)-2,2-dimethyl-cyclopropanecarboxylate, α-cyano-3-phenoxybenzyl 3-(2-chloro-3,3,3-tri-fluoroprop-1-enyl)-2,2-dimethylcyclopropanecarboxylate, α-cyano-3-phenoxy-benzyl N-(2-chloro-α,α,α-trifluoro-p-tolyl)valinate, α-cyano-3-phenoxybenzyl 4-(difluoromethoxy)-α-(1-methylethyl)benzeneacetate, α-cyano-3-phenoxy-benzyl 3-(2,2-dibromovinyl)-2,2-dimethylcyclopropanecarboxylate, α-cyano-4-fluoro-3-phenoxybenzyl 3-(2,2-dichlorovinyl)-2,2-dimethylcyclopropane carboxylate and 2-(4-ethoxyphenyl)-2-methylpropyl 3-phenoxybenzyl ether.

DETAILED DESCRIPTION OF THE INVENTION

The compound (I) is disclosed in WO 96/11909 and can be prepared by the process described therein.

All the pyrethroid compounds used in the present invention are well known in the art and can be prepared by the respective ordinary methods. Their commercially available optical isomers or mixtures thereof can also be used.

More particularly, α-cyano-3-phenoxybenzyl 2-(4-chlorophenyl)- 3-methylbutyrate is commercially available as the racemic modification, (RS)-α-cyano-3-phenoxybenzyl (RS)-2-(4-chlorophenyl)-3-methylbutyrate [fenvalerate], or as the optical isomer, (S)-α-cyano-3-phenoxybenzyl (S)-2-(4-chlorophenyl)-3-methylbutyrate [esfenvalerate]; α-cyano-3-phenoxybenzyl 2,2,3,3-tetramethylcyclopropanecarboxylate is available as (RS)-α-cyano-3-phenoxybenzyl 2,2,3,3-tetramethylcyclopropanecarboxylate [fenpropathrin]; α-cyano-3-phenoxybenzyl 3-(2,2-dichlorovinyl)-2,2-dimethylcyclopropanecarboxylate is available as (RS)-α-cyano-3-phenoxybenzyl (1RS)-cis,trans-3-(2,2-dichlorovinyl)-2,2-dimethylcyclopropanecarboxylate [cypermethrin], a racemate of (S)-α-cyano-3-phenoxybenzyl (1R)-cis-3-(2,2-dichlorovinyl)-2,2-dimethylcyclopropanecarboxylate and (R)-α-cyano-3-phenoxybenzyl (1S)-cis-3-(2,2-dichlorovinyl)-2,2-dimethylcyclopropanecarboxylate [alpha-cypermethrin], a mixture of two enantiomeric pairs, {(S)(1R)-cis and (R)(1S)-cis with (S)(1R)-trans and (R)(1S)-trans} [beta-cypermethrin], or (S)-α-cyano-3-phenoxybenzyl (1RS)-cis,trans-3-(2,2-dichlorovinyl)-2,2-dimethylcyclopropanecarboxylate [zeta-cypermethrin]; α-cyano-3-phenoxybenzyl 3-(2-chloro-3,3,3-trifluoroprop-1-enyl)-2,2-dimethylcyclopropanecarboxylate is available as (RS)-α-cyano-3-phenoxybenzyl (Z)-(1RS)-cis-3-(2-chloro-3,3,3-trifluoroprop-1-enyl)-2,2-dimethylcyclopropanecarboxylate [cyhalothrin] or a mixture of (S)-α-cyano-3-phenoxybenzyl (Z)-(1R)-cis-3-(2-chloro-3,3,3-trifluoroprop-1-enyl)-2,2-dimethylcyclopropanecarboxylate and (R)-α-cyano-3-phenoxybenzyl (Z)-(1S)-cis-3-(2-chloro-3,3,3-trifluoroprop-1-enyl)-2,2-dimethylcyclopropanecarboxylate [lambda-cyhalothrin]; α-cyano-3-phenoxybenzyl N-(2-chloro-α,α,α-trifluoro-p-tolyl)valinate is available as (RS)-α-cyano-3-phenoxybenzyl N-(2-chloro-α,α,α-trifluoro-p-tolyl)-D-valinate [tau-fluvalinate]; α-cyano-3-phenoxybenzyl 4-(difluoromethoxy)-α-(1-methylethyl)benzeneacetate is available as (RS)-α-cyano-3-phenoxybenzyl (S)-4-(difluoromethoxy)-α-(1-methylethyl)benzeneacetate [flucythrinate]; α-cyano-3-phenoxybenzyl 3-(2,2-dibromovinyl)-2,2-dimethylcyclopropanecarboxylate is available as (S)-α-cyano-3-phenoxybenzyl (1R)-cis-3-(2,2-dibromovinyl)-2,2-dimethylcyclopropanecarboxylate [deltamethrin]; α-cyano-4-fluoro-3-phenoxybenzyl 3-(2,2-dichlorovinyl)-2,2-dimethylcyclopropanecarboxylate is available as (RS)-α-cyano-4-fluoro-3-phenoxybenzyl (1RS)-cis,trans-3-(2,2-dichlorovinyl)-2,2-dimethylcyclopropanecarboxylate [cyfluthrin] or a mixture of two enantiomeric pairs, {(S)(1R)-cis and (R)(1S)-cis with (S)(1R)-trans and (1R)(1S)-trans} [beta-cyfluthrin]; and 2-(4-ethoxyphenyl)-2-methylpropyl 3-phenoxybenzyl ether is commercially available under the common name, etofenprox.

The pests which can be controlled by the pesticidal composition of the present invention may include, for example, arthropods as recited below:

Hemiptera:

Delphacidae such as *Laodelphax striatellus, Nilaparvata lugens* and *Sogatella furcifera*; Deltocephalidae such as *Nephotettix cincticeps* and *Empoasca onukii*; Aphididae such as *Aphis gossypii* and *Myzus persicae*; Pentatomidae; Aleyrodidae such as *Trialeurodes vaporariorum, Bemisia tabaci* and *Bemisia argentifolii*; Coccidae; Tingidae; Psyllidae, etc.

Lepidoptera:

Pyralidae such as *Chilo suppressalis, Cnaphalocrocis medinalis, Ostrinia nubilalis* and *Parapediasia teterrella*; Noctuidae such as *Spodoptera litura, Spodoptera exigua, Pseudaletia separata, Mamestra brassicae, Agrotis ipsilon*, Trichoplusia spp., Heliothis spp., Helicoverpa spp. and Earias spp.; Pieridae such as *Pieris rapae crucivora*; Tortricidae such as *Adoxophyes orana fasciata, Grapholita molesta* and *Cydia pomonella*; Carposinidae such as *Carposina niponensis*; Lyonetiidae such as *Lyonetia clerkella*; Gracillariidae such as *Phyllonorycter ringoniella*; Phyllocnistidae such as *Phyllocnistis citrella*; Yponomeutidae such as *Plutella xylostella*; Gelechiidae such as *Pectinophora gossypiella*; Arctiidae; Tineidae, etc.

Diptera:

Calicidae, Aedes spp., Anopheles spp., Chironomidae, Muscidae, Calliphoridae, Sarcophagidae, Anthomyiidae, Cecidomyiidae, Agromyzidae, Tephritidae, Drosophilidae, Psychodidae, Simuliidae, Tabanidae, Stomoxyidae, etc.

Coleoptera:

Chrysomelidae, Scarabaeidae, Curculionidae, Attelabidae, Coccinellidae, Ceramhycidae, Tenebrionidae, etc.

Thysanoptera:

Thripidae such as Thrips spp., e.g., *Thrips palmi*, Frankliniella spp., e.g., *Frankliniella occidentalis*, Sciltothrips spp., e.g., *Sciltothrips dorsalis*; and Phlaeotheripidae, etc.

Hymenoptera:

Tenthredinidae, Formicidae, Vespidae, etc.

Dictyoptera:

Blattidae, Blattellidae, etc.

Orthoptera:

Acrididae, Gryllotalpidae, etc.

Aphaniptera:

Purex irritans etc.

Anoplura:

Pediculus human us capitis etc.

Acarina:

Tetranychidae such as Tetranychus spp. and Panonychus spp.; Tarsonemidae; Eriophyidae; Acaridae; Ixodidae, etc.

In the pesticidal composition of the present invention, the mixing ratio of compound (I) and the pyrethroid compound is usually in the range of from 0.5:99.5 to 99.5:0.5 by weight, preferably from 1:99 to 98:2 by weight, and more preferably from 1:70 to 90:10 by weight.

The pesticidal composition of the present invention usually contains compound (I), a pyrethroid compound and an inert carrier, and is obtainable by mixing compound (I) with the pyrethroid compound; mixing it with solid carries, liquid carries, gaseous carriers, baits or others; adding, if necessary, surfactants and other auxiliaries; and formulating the mixture into various forms such as oil sprays, emulsifiable concentrates, wettable powders, flowables, granules, dusts, aerosols, fumigants (e.g., foggings) or poison baits.

In these formulations, compound (I) and the pyrethroid compound as the active ingredients are usually contained at 0.01% to 95% by weight.

The solid carrier which can be used in the formulation may include, for example, fine powder or granules of clay materials such as kaolin clay, diatomaceous earth, synthetic hydrated silicon oxide, bentonite, Fubasami clay and acid clay; various kinds of talc, ceramics, and other inorganic minerals such as sericite, quartz, sulfur, activated carbon, calcium carbonate and hydrated silica; and chemical fertilizers such as ammonium sulfate, ammonium phosphate, ammonium nitrate, urea and ammonium chloride.

The liquid carrier may include, for example, water; alcohols such as methanol and ethanol; ketones such as acetone and methyl ethyl ketone; hydrocarbons such as hexane, cyclohexane, kerosene and light oil; esters such as ethyl acetate and butyl acetate; nitrites such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil.

The gaseous carrier or propellant may include, for example, Freon gas, butane gas, LPG liquefied petroleum gas), dimethyl ether, and carbon dioxide.

The surfactant may include, for example, alkyl sulfates, alkyl sulfonates, alkyl arylsulfonates, alkyl aryl ethers and their polyoxyethylene derivatives, polyethylene glycol ethers, polyhydric alcohol esters, and sugar alcohol derivatives.

The auxiliaries such as fixing agents or dispersing agents may include, for example, casein, gelatin, polysaccharides such as starch, gum arabic, cellulose derivatives and alginic acid; lignin derivatives, bentonite, sugars, and synthetic water-soluble polymers such as polyvinyl alcohol, polyvinyl pyrrolidone and polyacrylic acid.

The stabilizer may include, for example, PAP (isopropyl acid phosphate), BHT (2,6-di-tert-butyl-4-methylphenol), BHA (mixtures of 2-tert-butyl-4-methoxyphenol and 3-tert-butyl-4-methoxyphenol), vegetable oils, mineral oils, surfactants, fatty acids, and their esters.

The base material for used in poison baits may include, for example, bait materials such as grain powder, vegetable oils, sugars and crystalline cellulose; antioxidants such as dibutylhydroxytoluene and nordihydroguaiaretic acid; preservatives such as dehydroacetic acid; substances for preventing erroneous eating, such as red pepper powder; and attractant flavors such as cheese flavor and onion flavor.

The pesticidal composition of the present invention can also be prepared by separately formulating the active ingredients according to a technique as described above, and then mixing these formulations with each other.

The pesticidal composition of the present invention, thus formulated, is used as such or after diluted with water. Furthermore, it may be used in admixture with, or separately but simultaneously with, other insecticides, nematocides, acaricides, bactericides, fungicides, herbicides, plant growth regulators, synergists, fertilizers, soil conditioners and/or animal feeds.

When the pesticidal composition of the present invention is used for agriculture, the application amount thereof is usually in the range of 0.1 to 100 g per 10 ares. In the case of emulsifiable concentrates, wettable powders, flowables, or similar formulations, which are used after diluted with water, the application concentration thereof is usually in the range of 1 to 10,000 ppm. In the case of granules, dusts, or similar formulations, they are applied as such formulations without any dilution. When the pesticidal composition of the present invention is used for epidemic prevention, it is usually applied after diluted with water to a concentration of 0.1 to 500 ppm in the case of emulsifiable concentrates, wettable powders, flowables, or similar formulations; or it is applied as such in the case of oil sprays, aerosols, fumigants, poisonous baits, or similar formulations.

The application amount and concentration may vary depending upon the conditions including types of formulations, times, places and methods of application, kinds of pests, and degree of damage, and they can be increased or decreased without limitation to the above range.

EXAMPLES

The present invention will be further illustrated by the following Formulation Examples and Test Examples; however, the present invention is not limited to these Examples.

The following are Formulation Examples, where parts are by weight.

Formulation Example 1
Emulsifiable concentrates

First, 10 parts of compound (I) and 2.5 parts of fenvalerate, esfenvalerate, fenpropathrin, cypermethrin, alpha-cypermethrin, beta-cypermethrin, zeta-cypermethrin, cyhalothrin, lambda-cyhalothrin, tau-fluvalinate, flucythrinate, deltamethrin, cyfluthrin, beta-cyfluthrin or etofenprox are dissolved in 35 parts of xylene and 35 parts of dimethylformamide, to which 11.5 parts of polyoxyethylene styryl phenyl ether and 6 parts of calcium dodecylbenzenesulfonate are added, and the mixture is well stirred to give an emulsifiable concentrate.

Formulation Example 2
Wettable powders

First, 10 parts of compound (I) and 2.5 parts of fenvalerate, esfenvalerate, fenpropathrin, cypermethrin, alpha-cypermethrin, beta-cypermethrin, zeta-cypermethrin, cyhalothrin, lambda-cyhalothrin, tau-fluvalinate, flucythrinate, deltamethrin, cyfluthrin, beta-cyfluthrin or etofenprox are added to a mixture of 4 parts of sodium laurylsulfate, 2 parts of calcium lignin sulfonate, 20 parts of synthetic hydrated silicon oxide fine powder and 61.5 parts of diatomaceous earth, and the mixture is well stirred to give a wettable powder.

Formulation Example 3
Granules

To 2.5 parts of compound (I) and 2.5 parts of fenvalerate, esfenvalerate, fenpropathrin, cypermethrin, alpha-cypermethrin, beta-cypermethrin, zeta-cypermethrin, cyhalothrin, lambda-cyhalothrin, tau-fluvalinate, flucythrinate, deltamethrin, cyfluthrin, beta-cyfluthrin or etofenprox are added 5 parts of synthetic hydrated silicon oxide fine powder, 5 parts of sodium dodecylbenzenesulfonate, 30 parts of bentonite and 55 parts of clay, and the mixture is well stirred. A suitable amount of water is added to the mixture, which is further stirred, granulated with a granulator, and air-dried to give a granule.

Formulation Example 4
Dusts

First, 0.5 part of compounds (I), 0.5 part of fenvalerate, esfenvalerate, fenpropathrin, cypermethrin, alpha-cypermethrin, beta-cypermethrin, zeta-cypermethrin, cyhalothrin, lambda-cyhalothrin, tau-fluvalinate, flucythrinate, deltamethrin, cyfluthrin, beta-cyfluthrin or etofenprox, 1 part of synthetic hydrated silicon oxide fine powder, 1 part of driless B (from Sankyo Co., Ltd.) as an aggregating agent, and 7 parts of clay are well mixed in a mortar and then stirred with a mixer. To the mixture is added 90 parts of cut-clay, and the mixture is well stirred to give a dust.

Formulation Example 5
Flowables

First, 10 parts of compound (1), 2.5 parts of fenvalerate, esfenvalerate, fenpropathrin, cypermethrin, alpha-cypermethrin, beta-cypermethrin, zeta-cypermethrin, cyhalothrin, lambda-cyhalothrin, tau-fluvalinate, flucythrinate, deltamethrin, cyfluthrin, beta-cyfluthrin or etofenprox, and 1.5 parts of sorbitan trioleate are mixed with 26 parts of an aqueous solution containing 2 parts of polyvinyl alcohol. The mixture is pulverized into fine particles with a particle size of not more than 3 $\mu$m with a sand grinder, to which 50 parts of an aqueous solution containing 0.05 part of xanthan gum and 0.1 part of aluminum magnesium silicate is added and 10 parts of propylene glycol is then added. The mixture is stirred to give a flowable.

Formulation Example 6
Oil Sprays

First, 0.1 part of compound (I) and 0.1 part of fenvalerate, esfenvalerate, fenpropathrin, cypermethrin, alpha-cypermethrin, beta-cypermethrin, zeta-cypermethrin, cyhalothrin, lambda-cyhalothrin, tau-fluvalinate, flucythrinate, deltamethrin, cyfluthrin, beta-cyfluthrin or etofenprox are dissolved in 5 parts of xylene and 5 parts of trichloroethane. The solution is mixed with 89.8 parts of deodorized kerosine to give an oil spray.

Formulation Example 7
Oil-based Aerosols

First, 0.5 part of compound (I), 0.5 part of fenvalerate, esfenvalerate, fenpropathrin, cypermethrin, alpha-cypermethrin, beta-cypermethrin, zeta-cypermethrin, cyhalothrin, lambda-cyhalothrin, tau-fluvalinate, flucythrinate, deltamethrin, cyfluthrin, beta-cyfluthrin or etofenprox, 10 parts of trichloroethane and 59 parts of deodorized kerosine are mixed to make a solution. The solution is put in an aerosol vessel. The vessel is equipped with a valve, through which 30 parts of a propellant (liquefied petroleum gas) is charged under increased pressure to give an oil-based aerosol.

Formulation Example 8
Water-based Aerosols

An aerosol vessel is filled with a mixture of 0.1 part of compound (I), 0.1 part of fenvalerate, esfenvalerate, fenpropathrin, cypermethrin, alpha-cypermethrin, beta-cypermethrin, zeta-cypermethrin, cyhalothrin, lambda-cyhalothrin, tau-fluvalinate, flucythrinate, deltamethrin, cyfluthrin, beta-cyfluthrin or etofenprox, 5 parts of xylene, 3.8 parts of deodorized kerosine and 1 part of an emulsifier (ATMOS 300 available from Atlas Chemical Co.); and 50 parts of pure water. The vessel is equipped with a valve, through which 40 parts of a propellant (liquefied petroleum gas) are charged under increased pressure to give a water-based aerosol.

Formulation Example 9

Emulsifiable Concentrate

First, 20 parts of compound (I) and 5 parts of cypermethrin are dissolved in 27.5 parts of xylene and 27.5 parts of dimethylformamide, to which 14 parts of polyoxyethylene styryl phenyl ether and 6 parts of calcium dodecylbenzenesulfonate are then added, and the mixture is well stirred to give an emulsifiable concentrate.

Formulation Example 10

Emulsifiable Concentrate

First, 0.156 part of compound (I) and 20 parts of etofenprox are dissolved in 30 parts of xylene and 30 parts of dimethylformamide, to which 14 parts of polyoxyethylene styryl phenyl ether and 5.844 parts of calcium dodecylbenzenesulfonate are then added, and the mixture is well stirred to give an emulsifiable concentrate.

The following Test Examples shows that the pesticidal composition of the present invention exhibits excellent pest-control effects.

In general, the pest-control effects expected, if there is no joint action, when two kinds of prescribed active ingredients are applied in admixture, are calculated by the following equation:

$$E = X + Y - \frac{X \times Y}{100}$$

where X is the mortality, mortality including moribundity, damage-inhibitory rate, or control value (%) when active compound A is applied at M ppm; Y is the mortality, mortality including moribundity, damage-inhibitory rate, or control value (%) when active compound B is applied at N ppm; and E is the mortality, mortality including moribundity, damage-inhibitory rate, or control value (%) when active compounds A and B are applied at M ppm and at N ppm, respectively.

Test Example 1: Damage-inhibitory test against *Helicoverpa armigera* (pest line resistant to synthetic pyrethroid agents)

Into an aqueous dilution of a test compound(s) formulation obtained according to Formulation Example 1 were immersed some four-instar larvae of *Helicoverpa armigera* for 5 seconds, followed by the removal of excess water with filter paper. These larvae were then given untreated cotton leaf chips (diameter, 1 cm) for feeding. Ten larvae were used for each treatment. After 24 hours, the degree of damage by eating on the cotton leaf chips was evaluated on the criteria recited below, and the damage-inhibitory rate was determined by the following equation:

$$\text{Damage-inhibitory rate (\%)} = \frac{\text{Damage of untreated leaf chips} - \text{Damage of treated leaf chips}}{\text{Damage of untreated leaf chips}} \times 100$$

Criteria for the degree of damage by eating: 0=0% damaged area; 1=from 1% to 10% damaged area; 2=from 11% to 20% damaged area; 3=from 21% to 30% damaged area; 4=from 31% to 40% damaged area; 5=from 41% to 50% damaged area; 6=from 51% to 60% damaged area; 7=from 61% to 70% damaged area; 8=from 71% to 80% damaged area; 9=from 81% to 90% damaged area; and 10=from 91% to 100% damaged area. Each value of percent damaged area was rounded off to the first decimal point.

The results are shown in Table 1 below.

TABLE 1

| Test compounds | Application concentration (ppm) | Damage-inhibitory rate calculated (%) | Damage-inhibitory rate found (%) |
|---|---|---|---|
| (I) | 100 | | 65 |
| esfenvalerate | 25 | | 21 |
| (I) + esfenvalerate | 100 + 25 | 68 | 92 |
| (I) | 100 | | 49 |
| fenvalerate | 25 | | 10 |
| (I) + fenvalerate | 100 + 25 | 54 | 98 |
| (I) | 100 | | 78 |
| flucythrinate | 25 | | 6 |
| (I) + flucythrinate | 100 + 25 | 79 | 90 |
| (I) | 100 | | 75 |
| tau-fluvalinate | 25 | | 7 |
| (I) + tau-fluvalinate | 100 + 25 | 77 | 95 |
| (I) | 50 | | 61 |
| fenpropathrin | 100 | | 28 |
| (I) + fenpropathrin | 50 + 100 | 72 | 94 |

Test Example 2: Damage-inhibitory test against *Helicoverpa armigera* (pest line resistant to synthetic pyrethroid agents)

First, 10 parts of compound (I) was dissolved in 37 parts of xylene and 37 parts of dimethylformamide, to which 10 parts of polyoxyethylene styryl phenyl ether and 6 parts of calcium dodecylbenzenesulfonate were added, and the mixture was well stirred to give an emulsifiable concentrate.

An aqueous dilution of the emulsifiable concentrate was mixed with an aqueous dilution of a commercially available emulsifiable concentrate of permethrin (trade name, Adion; from Sumitomo Chemical Co., Ltd.) or cypermethrin (trade name, Agrothrin; from Sumitomo Chemical Co., Ltd.) to have a prescribed concentration.

Into the dilution were immersed some four-instar larvae of *Helicoverpa armigera* for 5 seconds, followed by the removal of excess water with filter paper. These larvae were then given untreated cotton leaf chips for feeding. Ten larvae were used for each treatment. After 24 hours, the degree of damage by eating on the cotton leaf chips was evaluated on the criteria recited below, and the damage-inhibitory rate was determined by the following equation:

$$\text{Damage-inhibitory rate (\%)} = \frac{\text{Damage of untreated leaf chips} - \text{Damage of treated leaf chips}}{\text{Damage of untreated leaf chips}} \times 100$$

Criteria for the degree of damage by eating: 0=0% damaged area; 1=from 1% to 10% damaged area; 2=from 11% to 20% damaged area; 3=from 21% to 30% damaged area; 4=from 31% to 40% damaged area; 5=from 41% to 50% damaged area; 6=from 51% to 60% damaged area; 7=from 61% to 70% damaged area; 8=from 71% to 80% damaged area; 9=from 81% to 90% damaged area; and 10=from 91% to 100% damaged area. Each value of percent damaged area was rounded off to the first decimal point.

The results are shown in Table 2 below.

TABLE 2

| Test compounds | Application concentration (ppm) | Damage-inhibitory rate calculated (%) | Damage-inhibitory rate found (%) |
| --- | --- | --- | --- |
| (I) | 25 | | 15 |
| permethrin | 50 | | 19 |
| (I) + permethrin | 25 + 50 | 31 | 92 |
| (I) | 100 | | 64 |
| cypermethrin | 30 | | 0 |
| (I) + cypermethrin | 100 + 30 | 64 | 92 |
| (I) | 100 | | 64 |
| cypermethrin | 60 | | 34 |
| (I) + cypermethrin | 100 + 60 | 76 | 96 |

Test Example 3: Insecticidal test against *Plutella xylostella* (pest line resistant to organic phosphorous agents, synthetic pyrethroid agents and other agents)

To an aqueous dilution of a test compound(s) formulation obtained according to Formulation Example 1 was added a spreading agent (New RINOU available from Nihon Noyaku K.K.) at a dilution ratio of 3000-fold. The dilution was sprayed over potted cabbages at the four to five leaf stage at a volume of 25 ml per pot. After the treated plants were air dried, twenty third-instar larvae of *Plutella xylostella* were set free on each pot. After 5 days, the mortality was determined.

The results are shown in Table 3 below.

TABLE 3

| Test compounds | Application concentration (ppm) | Mortality calculated (%) | Mortality found (%) |
| --- | --- | --- | --- |
| (I) | 3.13 | | 40 |
| esfenvalerate | 6.25 | | 25 |
| (I) + esfenvalerate | 3.13 + 6.25 | 55 | 75 |
| (I) | 3.13 | | 40 |
| cyhalothrin | 25 | | 60 |
| (I) + cyhalothrin | 3.13 + 25 | 76 | 100 |
| (I) | 1.56 | | 15 |
| fenpropathrin | 100 | | 25 |
| (I) + fenpropathrin | 1.56 + 100 | 36 | 80 |

Test Example 4: Insecticidal test against Helicoverpa armigera (pest line resistant to synthetic pyrethroid agents)

First, 10 parts of compound (I) was dissolved in 37 parts of xylene and 37 parts of dimethylformamide, to which 10 parts of polyoxyethylene styryl phenyl ether and 6 parts of calcium dodecylbenzenesulfnonate were added, and the mixture was well stirred to give an emulsifiable concentrate.

An aqueous dilution of the emulsifiable concentrate was mixed with an aqueous dilution of a commercially available emulsifiable concentrate of lambda-cyhalothrin (trade name, Karate; from Imperial Chemical Industries Ltd.), deltamethrin (trade name, Decis; from Hoechst AG) or Cyfluthrin (trade name, Baythroid; from Bayer AG) to have a prescribed concentration.

Into the dilution were immersed some four-instar larvae of *Helicoverpa armigera* for 5 seconds, followed by the removal of excess water with filter paper. These larvae were then given untreated cotton leaf chips for feeding. Ten larvae were used for each treatment. After 24 hours, the mortality including moribundity was determined.

The results are shown in Table 4 below.

TABLE 4

| Test compounds | Application concentration (ppm) | Mortality including moribundity calculated (%) | Mortality including moribundity found (%) |
| --- | --- | --- | --- |
| (I) | 50 | | 40 |
| lambda-cyhalothrin | 25 | | 60 |
| (I) + lambda-cyhalothrin | 50 + 25 | 76 | 100 |
| (I) | 50 | | 40 |
| deltamethrin | 25 | | 20 |
| (I) + deltamethrin | 50 + 25 | 52 | 90 |
| (I) | 100 | | 40 |
| cyfluthrin | 50 | | 40 |
| (I) + cyfluthrin | 100 + 50 | 64 | 100 |

What is claimed is:

1. A pesticidal composition which comprises synergistic effective amount of 3,5-dichloro-1-(3,3-dichloro-2-propenyloxy)-4-[3-(5-trifluoromethylpyridin-2-yloxy)propoxy] benzene of the formula:

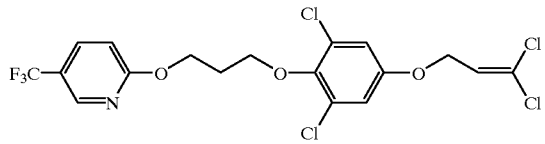

and a pyrethroid compound selected from the group consisting of α-cyano-3-phenoxybenzyl 2-(4-chlorophenyl)-3-methylbutyrate, α-cyano-3-phenoxybenzyl 2,2,3,3-tetramethylcyclopropanecarboxylate, α-cyano-3-phenoxybenzyl 3-(2,2-dichlorovinyl)-2,2-dimethylcyclopropanecarboxylate, α-cyano-3-phenoxybenzyl 3-(2-chloro-3,3,3-trifluoroprop-1-enyl)-2,2-dimethylcyclopropanecarboxylate, α-cyano-3-phenoxybenzyl N-(2-chloro-α,α, α-trifluoro-p-tolyl) valinate, α-cyano-3-phenoxybenzyl 4-(difluoromethoxy)-α-(1-methylethyl)benzeneacetate, α-cyano-3-phenoxybenzyl 3-(2,2-dibromovinyl)-2,2-dimethylcyclopropanecarboxylate, α-cyano-4-fluoro-3-phenoxybenzyl 3-(2,2-dichlorovinyl)-2,2-dimethylcyclopropanecarboxylate and 2-(4-ethoxyphenyl)-3-phenoxybenzyl ether, as active ingredients, and a carrier.

2. A pesticidal composition according to claim 1, wherein the mixing ratio of 3,5-dichloro-1-(3,3-dichloro-2-propenyloxy)-4-[3-(5-trifluoromethylpyridin-2-yloxy)propoxy]benzene and the pyrethroid compound is from 0.5:99.5 to 99.5:0.5 by weight.

3. A pesticidal composition according to claim 1, wherein the pyrethroid compound is α-cyano-3-phenoxybenzyl 2-(4-chlorophenyl)-3-methylbutyrate.

4. A pesticidal composition according to claim 1, wherein the pyrethroid compound is α-cyano-3-phenoxybenzyl 2,2,3,3-tetramethylcyclopropanecarboxylate.

5. A pesticidal composition according to claim 1, wherein the pyrethroid compound is α-cyano-3-phenoxybenzyl 3-(2,2-dichlorovinyl)-2,2-dimethylcyclopranecarboxylate.

6. A pesticidal composition according to claim 1, wherein the pyrethroid compound is α-cyano-3-phenoxybenzyl 3-(2-chloro-3,3,3-trifluoroprop-1-enyl)-2,2-dimethylcyclopropanecarboxylate.

7. A pesticidal composition according to claim 1, wherein the pyrethroid compound is α-cyano-3-phenoxybenzyl N-(2-chloro-α,α,α-tri-fluoro-p-tolyl)valinate.

8. A pesticidal composition according to claim 1, wherein the pyrethroid compound is α-cyano-3-phenoxybenzyl 4-(difluoromethoxy)-α-(1-methylethyl)benzeneacetate.

9. A pesticidal composition according to claim 1, wherein the pyrethroid compound is α-cyano-3-phenoxybenzyl 3-(2,2-dibromovinyl)-2,2-dimethylcyclopropanecarboxylate.

10. A pesticidal composition according to claim 1, wherein the pyrethroid compound is α-cyano-4-fluoro-3-phenoxybenzyl 3-(2,2-dichloro-vinyl)-2,2-dimethylcyclopropanecarboxylate.

11. A pesticidal composition according to claim 1, wherein the pyrethroid compound is 2-(4-ethoxyphenyl)-2-methylpropyl 3-phenoxybenzyl ether.

12. A method for controlling pests, which comprises applying synergistic effective amounts of 3,5-dichloro-1-(3,3-dichloro-2-propenyloxy)-4-[3-(5-trifluoromethylpyridin-2-yloxy)propoxy]benzene of the formula:

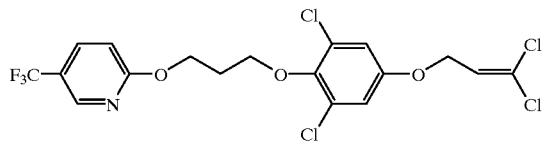

and a pyrethroid compound selected from the group consisting of α-cyano-3-phenoxybenzyl 2-(4-chlorophenyl)-3-methylbutyrate, α-cyano-3-phenoxybenzyl 2,2,3,3-tetramethylcyclopropanecarboxylate, α-cyano-3-phenoxybenzyl 3-(2,2-dichlorovinyl)-2,2-dimethylcyclopropanecarboxylate, α-cyano-3-phenoxybenzyl 3-(2-chloro-3,3,3-trifluoroprop-1-enyl)-2,2-dimethylcyclopropanecarboxylate, α-cyano-3-phenoxybenzyl N-(2-chloro-α,α,α-trifluoro-p-tolyl)valinate, α-cyano-3-phenoxybenzyl 4-(difluoromethoxy)-α-(1-methylethyl)benzeneacetate, α-cyano-3-phenoxybenzyl 3-(2,2-dibromovinyl)-2,2-dimethylcyclopropanecarboxylate, α-cyano-4-fluoro-3-phenoxybenzyl 3-(2,2-dichlorovinyl)-2,2-dimethylcyclopropanecarboxylate and 2-(4-ethoxyphenyl)-2-methylpropyl 3-phenoxybenzyl ether, to pests or a locus where the pests inhabit.

13. A method according to claim 12, wherein the application amount of 3,5-dichloro-1-(3,3-dichloro-2-propenyloxy)-4-[3-(5-trifluoromethylpyridin-2-yloxy)propoxy]benzene and the pyrethroid compound is within the ratio of from 0.5:99.5 to 99.5:0.5 by weight.

* * * * *